US00PP19249P2

(12) United States Plant Patent
Clifford et al.

(10) Patent No.: US PP19,249 P2
(45) Date of Patent: Sep. 16, 2008

(54) ***DIANTHUS* PLANT NAMED 'RED ROMANCE'**

(50) Latin Name: *Dianthus barbatus*
Varietal Denomination: Red Romance

(76) Inventors: John K. Clifford, Clifford's Perennial & Vine, Inc., P.O. Box 473, Paw Paw, MI (US) 49079; Ken J. Clifford, Clifford's Perennial & Vine, Inc., P.O. Box 473, Paw Paw, MI (US) 49079

( * ) Notice: Subject to any disclaimer, the term of this patent is extended or adjusted under 35 U.S.C. 154(b) by 0 days.

(21) Appl. No.: 11/974,997

(22) Filed: Oct. 17, 2007

(51) Int. Cl.
*A01H 5/00* (2006.01)

(52) U.S. Cl. ..... Plt./283

(58) Field of Classification Search ..... Plt./283
See application file for complete search history.

*Primary Examiner*—Annette H Para
(74) *Attorney, Agent, or Firm*—Penny J. Aguirre

(57) ABSTRACT

A new cultivar of *Dianthus barbatus,* 'Red Romance', a sport of *Dianthus barbatus* 'Heart Attack', characterized by its bright strawberry red flowers held on sturdy stems, its clean, deep green foliage, its perennial plant habit, and its vigorous growth habit.

2 Drawing Sheets

Botanical classification: *Dianthus barbatus.*
Variety denomination: 'Red Romance'.

BACKGROUND OF THE INVENTION

The present invention relates to a new and distinct cultivar of *Dianthus* plant, botanically known as *Dianthus barbatus* 'Red Romance' and will be referred to hereinafter by its cultivar name, 'Red Romance'. The new cultivar represents a new cultivar of sweet Williams, an herbaceous perennial grown for landscape use.

'Red Romance' was discovered in a container block in the inventor's nursery in Paw Paw, Mich. in May of 2007. The new cultivar derived as a naturally occurring branch mutation that arose during in vitro propagation of *Dianthus barbatus* 'Heart Attack' (not patented).

Asexual reproduction of the new cultivar was first accomplished using basal stem cuttings in June of 2007 in Paw Paw, Mich. The characteristics of this cultivar have been determined to be stable and are reproduced true to type in successive generations.

SUMMARY OF THE INVENTION

The following traits have been repeatedly observed and are determined to be the characteristics of the new cultivar. These attributes in combination distinguish 'Red Romance' as unique from all other varieties of *Dianthus* known to the inventor.

1. 'Red Romance' exhibits bright strawberry red colored flowers held on strong, upright stems.
2. 'Red Romance' exhibits clean, deep green, strap-like foliage.
3. 'Red Romance' has a vigorous growth habit.

'Red Romance' differs from its parent plant, 'Heart Attack' in having bright red flowers whereas 'Heart Attack' exhibits dark red flowers. 'Red Romance' is similar to 'Heart Attack' in other plant characteristics. *Dianthus barbatus* is typically grown as seed strains and few asexually propagated cultivars are available. Plants of *Dianthus barbatus* typically have a biennial plant habit or are short lived. 'Heart Attack' is unique for its true perennial nature, therefore 'Red Romance' promises the same perennial habit as 'Heart Attack'.

BRIEF DESCRIPTION OF THE DRAWING

The accompanying colored photographs illustrate the overall appearance and distinct characteristics of the new *Dianthus.* The photographs in the figures were taken of a plant about 14 months in age as grown outdoors in Paw Paw, Mich.

FIG. 1 shows the plant habit of 'Red Romance' in bloom while

Figure 1:
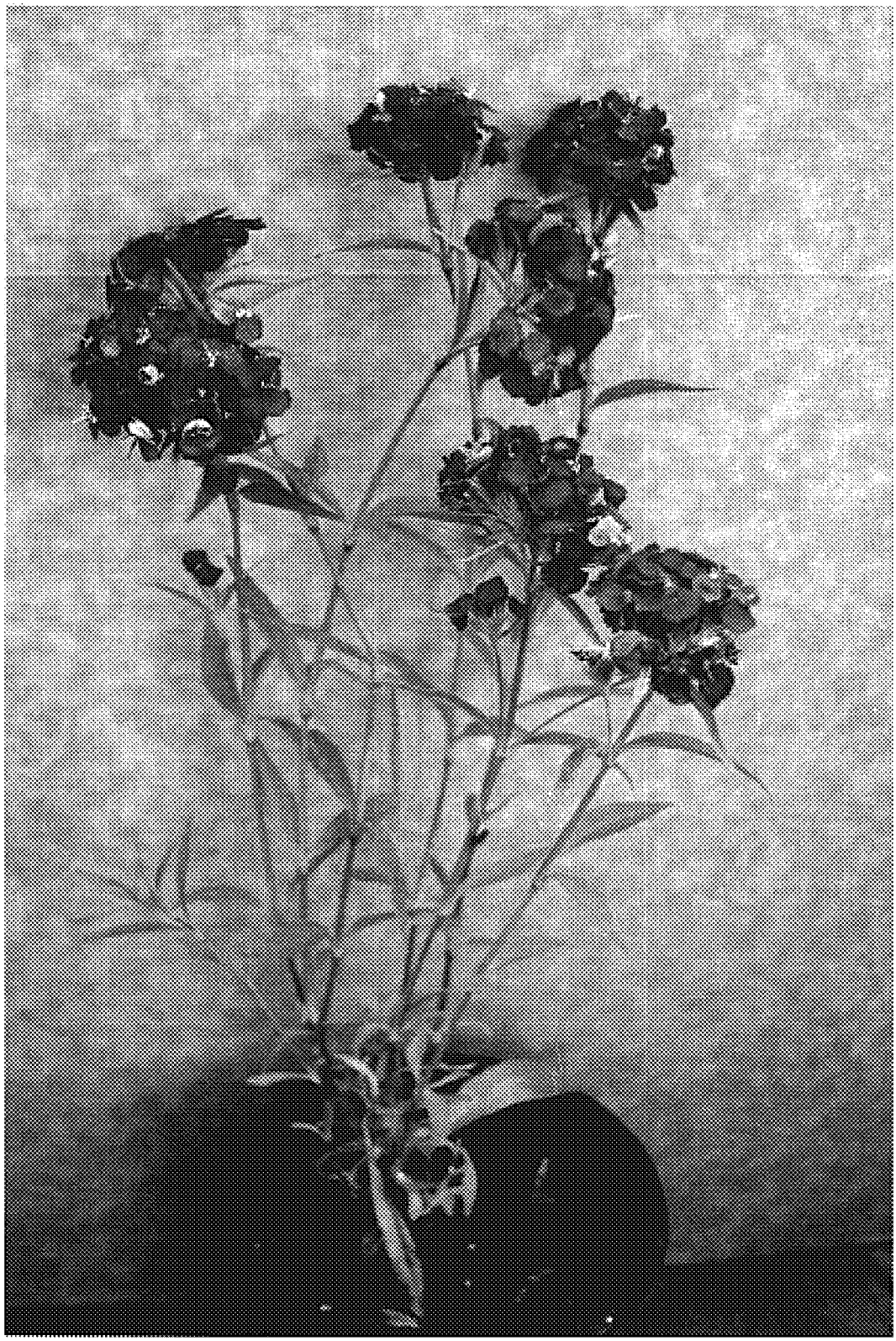
Figure 2:
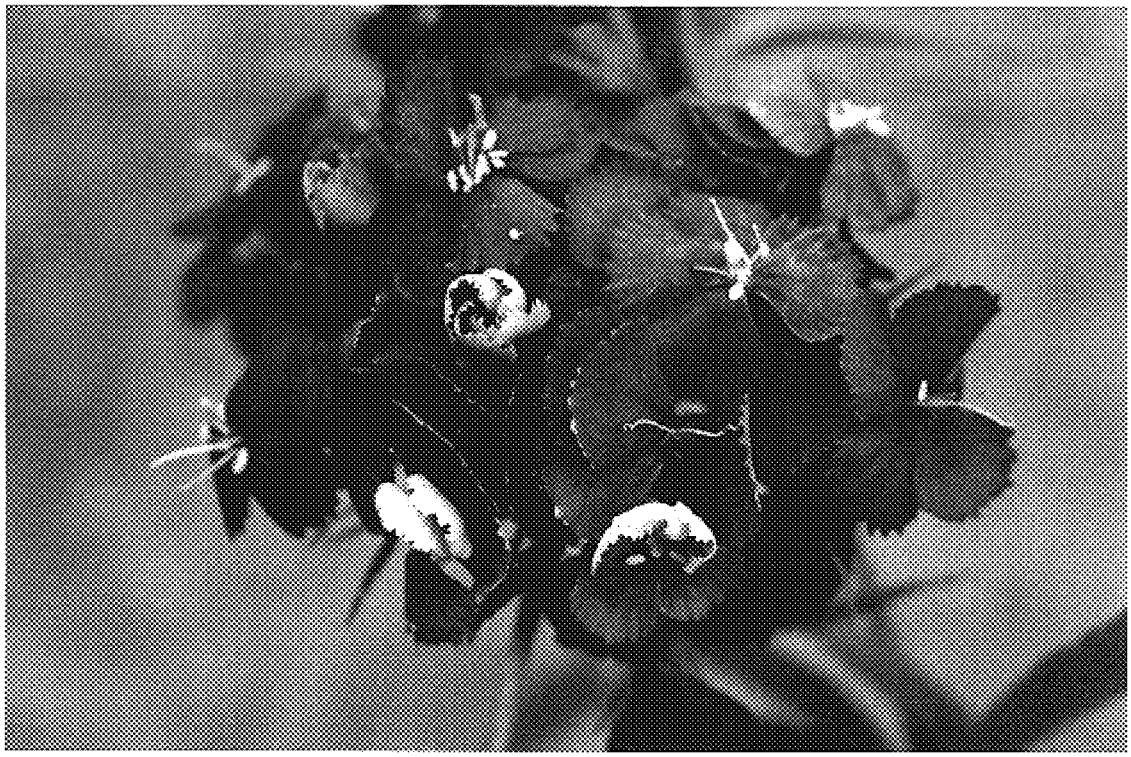
FIG. 2 is a close-up view of the flowers of 'Red Romance'.
Figure 3:
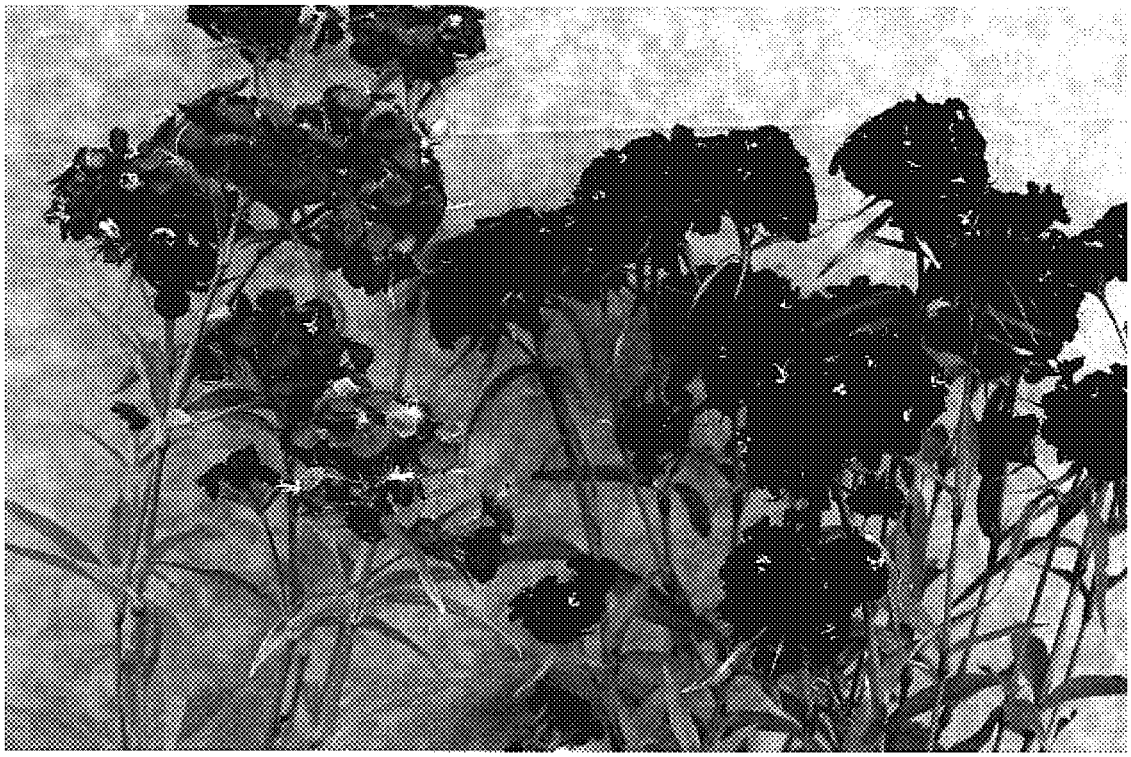

The photograph shown in FIG. 3 shows a comparison of the flowers of 'Red Romance' (shown on left) and 'Heart Attack' (shown on right).

The colors in the photographs are as close as possible with the photographic and printing technology utilized. The color values cited in the detailed botanical description accurately describe the colors of the new *Dianthus.*

DETAILED BOTANICAL DESCRIPTION

The following is a detailed description of a plant about 14 months in age of the new cultivar as grown outdoors in Paw Paw, Mich. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

General description:

*Blooming period.*—Blooms for about 3 weeks, beginning in late April in Michigan.

*Plant habit.*—Herbaceous perennial, upright.

*Height and spread.*—Matures to about 50 cm in height and about 25 cm in width.

*Hardiness.*—At least to U.S.D.A. Zones 4.

*Diseases and pests.*—No susceptibility or resistance to diseases or pests common to *Dianthus* has been observed.

*Root description.*—Fibrous.

Growth and propagation:

*Propagation.*—Basal stem cuttings.

*Root initiation.*—Basal stem cuttings root in about 20 days with rooting hormone under greenhouse conditions.

*Growth rate.*—Vigorous.

Stem description:

*Stem strength.*—Strong and held upright.

*Shape.*—Oval, solid swollen at nodes.

*Stem color.*—144A to 144B suffused with 183A on lower internodes.

*Stem size.*—Average of 2.2 mm in diameter and up to 38 cm in length.

*Stem surface.*—Puberulent.

*Branching habit.*—Branches emerge from congested whorl at base, no secondary branches without pinching.

Foliage description:

*Leaf division.*—Simple.

*Leaf shape.*—Lanceolate.

*Leaf base.*—Blunt, clasping to stem.

*Leaf apex.*—Acute.

*Leaf margin.*—Entire.

*Leaf venation.*—Tri-nerved, not conspicuous, color same as leaf color.

*Leaf attachment.*—Sessile, clasping.

*Leaf arrangement.*—Opposite.

*Leaf surface.*—Puberulent on upper and lower surfaces.

*Leaf color.*—Newly emerged and mature upper surface; between 146A and 144A with basal clasping portion suffused with 183A, newly emerged and mature lower surface; between 146B and 144A.

*Leaf size.*—Up to 5.5 cm in length and 1.5 cm in width with basal portion clasping leaf about 4 mm width and length.

*Foliage fragrance.*—None.

Flower description:

General description:

*Type.*—Compound corymb.

*Lastingness of inflorescence.*—About 3 weeks.

*Fragrance.*—Mildly sweet.

*Quantity of inflorescences.*—One terminal corymb with 1 to 2 smaller lateral corymbs.

*Corymb size.*—About 7 cm in diameter and 4 cm in depth for terminal corymbs, average of 3.2 cm in diameter and 3 cm in height for lateral corymbs.

*Flower type.*—Salviform.

*Flower size.*—About 2 cm in diameter and 2.5 cm in depth.

*Flower number.*—Average of 21 on terminal corymbs and 8 on lateral corymbs.

*Flower buds.*—About 2 cm in height and 3 mm in diameter, oblong in shape, color 144C with colored apex emerging 63B surrounded by narrow bracts 144C in color slightly suffused with 59B.

*Peduncle.*—Primary an average of 4 cm in length and 2.5 mm in diameter with laterals an average of 3.5 cm in length and 1 mm in width and within corymb about 5 mm in length and 1 mm in width, 144A in color, texture is puberulent.

*Pedicel.*—Flowers are sessile to peduncle.

*Petals.*—4, limb is obdeltoid in shape, glabrous surface, blunt apex with single notch, margins are serrated along apex and entire on sides, limb is about 1 cm in width and 8 mm in length, claw is about 1 cm in length and an average of 0.5 mm in width, claw is 144D in color, limb opens in a blend of 58B, 58C and 58D on upper side and 62C to 62D with slight margin of 58A on lower side, limb matures to 53B on upper surface and 50C on lower surface, base of limb in slightly bearded and matures to 53A in color.

*Calyx.*—Cylindrical in shape, fused sepals, notched apex, glabrous surface, 8 mm in length and 4 mm in width, 144C to 144D in color.

*Sepals.*—5, fused.

*Epicalyx.*—Involucre-like, about 10, thread-like, extend length of calyx.

*Leafy bracts.*—Present at base of primary peduncle and base of corymb, up to 5 cm in length and 1 cm in width, same color and surface as leaves.

Reproductive organs:

*Gynoecium.*—Pistil; 1 with 2 styles, about 2 cm in length at maturity, styles; 155D in color, crystalline in appearance, about 9 mm in length, stigma; 155D flushed with 63C in color and curled, ovary; superior, oblong in shape, 5 mm in length and 1 mm in width, 160A in color.

*Androcoecium.*—Stamens; 10, un-fused, about 1 cm in length, filament; 155D in color, about 9 mm in length, very fine and crystalline in appearance, anther; 155B in color, dorsifixed, about 1.5 mm in length and 1 mm in width, pollen; moderate in quantity and 158C in color.

*Fruit and seed.*—Fruit; a capsule with apical teeth, seeds; 4 to 5 per capsule, 202A in color, about 1.5 mm in width and 2 mm in length.

It is claimed:

1. A new and distinct cultivar of *Dianthus barbatus* plant named 'Red Romance' as herein illustrated and described.

* * * * *